(12) United States Patent
Pietrzkowski

(10) Patent No.: US 8,124,135 B2
(45) Date of Patent: Feb. 28, 2012

(54) COMPOSITIONS AND METHODS FOR REDUCTION OF LDL OXIDATION

(75) Inventor: Zbigniew Pietrzkowski, Dyer, IN (US)

(73) Assignee: VDF FutureCeuticals, Inc., Momence, IL (US)

( * ) Notice: Subject to any disclaimer, the term of this patent is extended or adjusted under 35 U.S.C. 154(b) by 304 days.

(21) Appl. No.: 11/914,854

(22) PCT Filed: May 24, 2006

(86) PCT No.: PCT/US2006/020246
§ 371 (c)(1),
(2), (4) Date: May 16, 2008

(87) PCT Pub. No.: WO2006/127903
PCT Pub. Date: Nov. 30, 2006

(65) Prior Publication Data
US 2009/0098225 A1    Apr. 16, 2009

Related U.S. Application Data

(60) Provisional application No. 60/684,575, filed on May 24, 2005.

(51) Int. Cl.
*A01N 65/00* (2009.01)
(52) U.S. Cl. .................................................. 424/725
(58) Field of Classification Search .................. None
See application file for complete search history.

(56) References Cited

U.S. PATENT DOCUMENTS

| | | | |
|---|---|---|---|
| 5,762,936 A | 6/1998 | Ronzio | |
| 6,869,621 B2 * | 3/2005 | Hwang et al. | ................ 424/725 |

FOREIGN PATENT DOCUMENTS

| | | |
|---|---|---|
| JP | 58179456 | 10/1983 |
| WO | 9800024 | 1/1998 |
| WO | 9800026 | 1/1998 |
| WO | 9809526 | 3/1998 |
| WO | 02060419 | 8/2002 |

* cited by examiner

*Primary Examiner* — Michael Meller
(74) *Attorney, Agent, or Firm* — Fish & Associates, PC

(57) ABSTRACT

Dicot, and especially Brassicaceae sprout preparations are employed as a dietary agents that significantly reduce oxidized species in human serum. In one especially preferred aspect, contemplated compositions are employed to reduce serum oxLDL and to increase serum HDL levels.

5 Claims, 2 Drawing Sheets

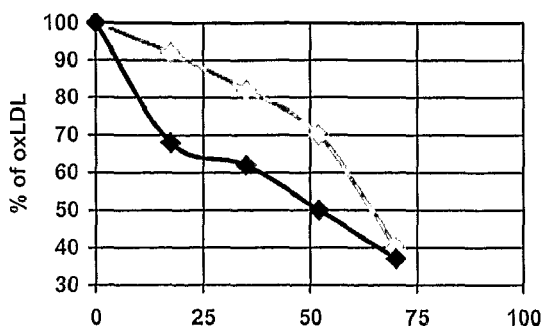
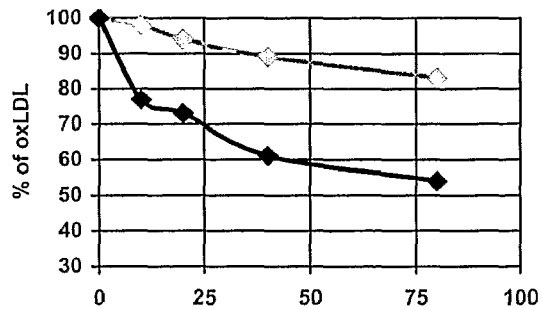
Figure 1A
Figure 1B
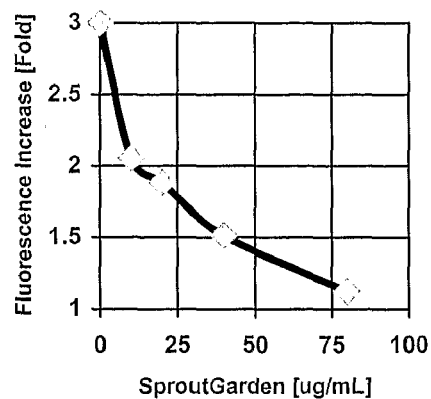
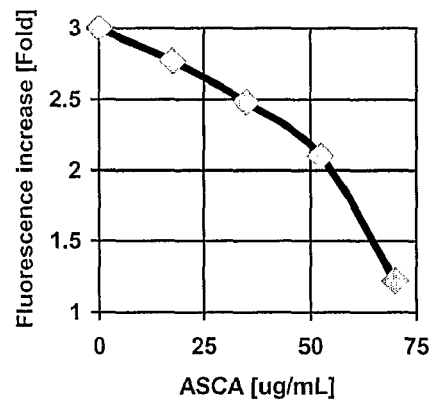
Figure 1C
Figure 1D
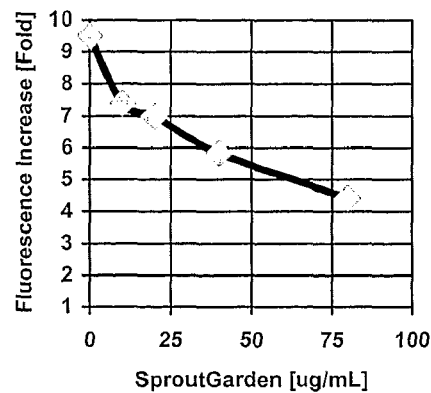
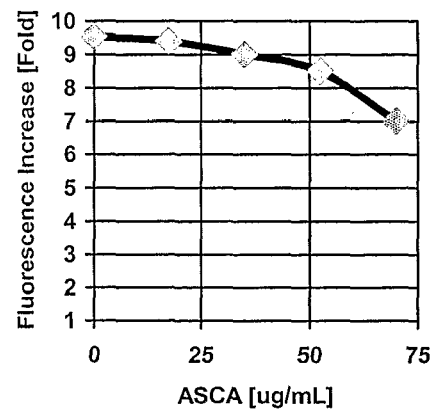
Figure 1E
Figure 1F

COMPOSITIONS AND METHODS FOR REDUCTION OF LDL OXIDATION

This application claims the benefit of our U.S. provisional application with the Ser. No. 60/684,575, which was filed May 24, 2005, and which is incorporated by reference herein.

FIELD OF THE INVENTION

The field of the invention is bioactive compositions and methods, and especially as they relate to reduction of LDL-oxidation in human.

BACKGROUND OF THE INVENTION

Among numerous other factors, oxidation of low-density lipoproteins (LDL) is frequently associated with arterial plaque build-up, which eventually may result in significant obstruction of a blood vessel and/or provide a source of material that can block downstream vasculature (see e.g., Biochem Soc Trans., 2001, 29, 358-362). Therefore, oxLDL has recently been proposed as a potential prognostic marker of cardiovascular conditions (see e.g., Meisinger et al., Circulation, 2005, 112, 651-657).

Use of antioxidants, and especially dietary antioxidants to prevent LDL oxidation appears to present an attractive alternative to pharmaceutical and/or interventional therapy. For example, polyphenols, tocopherol, and ascorbic acid were described as effective agents to reduce LDL-oxidation (see e.g., Eur J Pharmacol. 2005 Apr. 25; 513(3): 173-9), as well as gentisic acid, an aspirin metabolite, as described elsewhere (Eur J Pharmacol. 2005 Apr. 25; 513(3): 173-9). Isoflavones were reported as being at least somewhat effective as described in Am J Clin Nutr. 2005 January; 81(1):43-9. However, most of the isolated compounds available as over-the-counter compositions have one or more problems. For example, high-dose tocopherol administration has been reported as increasing the risk for certain neoplasms. Long-term administration of aspirin is typically associated with an increased risk of intestinal bleeding, and polyphenols, especially where administered in liquid oral formulation, tend to stain teeth, and isoflavones may exhibit estrogenic effects, especially at relatively high dosages. Moreover, initial and hopeful reports regarding the beneficial role of antioxidant vitamins against atherosclerosis were followed by the negative results of almost all large randomized trials (see e.g., Am J Physiol Heart Circ Physiol 282: H797-H802, 2002).

Therefore, it has been concluded that treatment with the antioxidant vitamins C and E is not recommended for prevention or treatment of coronary atherosclerosis dietary (see e.g., Herz, 2003, 28: 628-638).

In further known methods to reduce LDL oxidation, certain functional food products and supplements were described as reducing LDL oxidation at least to some degree. For example, selected pomegranate (see e.g., J Nat Prod., 2004, 67, 2096-8), almond (see e.g., Circulation, 2002, 106, 1327-32), and grape (see e.g., Free Radical Res., 2003, 37, 573-84) preparations were reported to have an effect of LDL oxidation. While such methods appear to hold at least some promise, availability, preparation, and economic factors associated with such materials often precluded successful marketing of these products and supplements. Moreover, the protective effect of these known preparations was at least in some cases less than desirable.

Therefore, while numerous compositions and methods are known in the art to reduce LDL oxidation, all or almost all of them suffer from one or more disadvantages. Thus, there is still a need to provide improved compositions and methods that reduce LDL oxidation, and most advantageously compositions and methods that also increase HDL levels.

SUMMARY OF THE INVENTION

The present invention is directed to compositions and methods to reduce the serum levels of oxidized species in a mammal (preferably a human), wherein the oxidized species particularly include oxLDL, lipid peroxides, carbonyl proteins, nitrosoproteins, etc. In still further preferred aspects, contemplated compositions will also raise serum HDL levels. Preferably, contemplated compositions include a combination of at least two distinct types of dicot (and most preferably cruciferous) sprouts in an amount effective to significantly reduce oxLDL levels when orally administered to a human at a daily dosage effective to reduce oxLDL.

In one aspect of the inventive subject matter, a method of reducing oxidized LDL cholesterol in serum of a human will include a step of providing a combination of at least two preparations of two distinct dicot sprouts in form of a dietary supplement. In another step, the combination is included in the supplement in an amount effective to reduce oxidized LDL cholesterol in human serum when orally administered to the human, and in yet a further step, the human is instructed to ingest the supplement at a recommended daily dosage that is effective to reduce oxidized LDL cholesterol in the human.

In especially preferred aspects, at least one of the two, and more typically both of the distinct dicot sprouts are cruciferous sprouts and may be selected from the group consisting of alfalfa, red clover, green cress, broccoli, cauliflower, Daikon radish, kale, yellow mustard, soy, lentil, and cabbage. However, in further aspects, one to seven additional distinct preparations from distinct dicot sprouts selected from the group consisting of alfalfa, red clover, green cress, broccoli, cauliflower, Daikon radish, kale, yellow mustard, soy, lentil, and cabbage may be included in the preparation.

It is further contemplated that at least one of the two and more typically all of the dicot sprout preparation comprises an at least partially dehydrated (e.g., air dried, freeze dried, drum dried, spray dried, dried using heat and/or partial vacuum, etc.) and powderized form of the dicot sprout. Such preparations may also include materials in which the sprout (in dried or native form) is processed to remove an undesirable ingredient and/or increase the concentration of a desirable ingredient. Typically, supplements comprising contemplated sprout preparations reduce oxidized LDL cholesterol by at least 20% when administered over at least 10 days, and/or increase HDL cholesterol by at least 6% when administered over at least 10 days. Thus, and viewed from another perspective, contemplated preparations are present in the supplement in an amount effective to increase the numerical ratio of HDL [mg/dl] to oxidized LDL [U/l] by at least 2%, more preferably at least 4%, even more preferably at least 6%, and most preferably at least 10%.

In another aspect of the inventive subject matter, a nutritional supplement product for measurable reduction of oxidized LDL cholesterol by at least 20% in human serum includes a combination of at least two preparations of two distinct dicot sprouts, wherein the combination is present in the supplement in an amount effective to reduce oxidized LDL cholesterol in human serum when orally administered to the human. Most typically, the product is associated with an information that oral administration of the supplement reduces oxidized LDL cholesterol.

Various objects, features, aspects and advantages of the present invention will become more apparent from the following detailed description of preferred embodiments of the invention along with the accompanying drawing.

BRIEF DESCRIPTION OF THE DRAWINGS

FIGS. 1A and 1B are graphs indicating reduction of ex vivo serum oxLDL in response to addition of contemplated compositions and ascorbic acid as control in a Cu-mediated in vitro system.

FIGS. 1C to 1F are graphs indicating reduction of in vivo serum oxLDL in response to oral administration of contemplated compositions and ascorbic acid as control in human.

DETAILED DESCRIPTION

Figure 2:
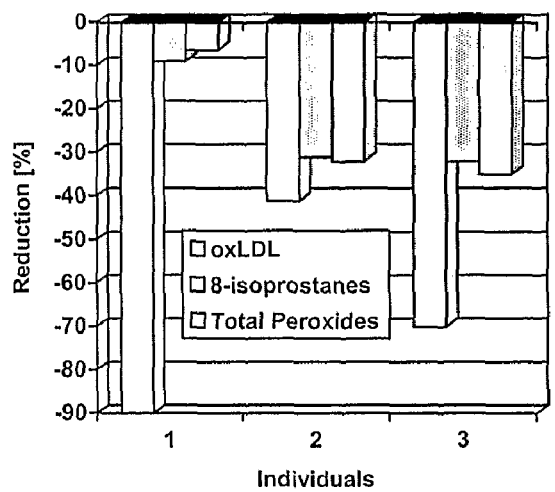
FIG. 2 is a graph indicating reduction of in vivo serum oxLDL and other oxidized species in response to oral administration of contemplated compositions in human.

The inventors have discovered that numerous sprout preparations, and particularly dicot sprout preparations (and among those, especially cruciferous sprout preparations) have a potent and reducing effect on LDL oxidation ex vivo as well as in vivo. Moreover, and in at least some dosages, contemplated preparations also significantly increased HDL levels in human serum in vivo. Therefore, the inventors contemplate various compositions and methods in which dicot, and especially cruciferous sprout preparations are employed to reduce in vivo LDL oxidation in human using oral administration of such preparations.

In one exemplary aspect of the inventive subject matter, a sprout preparation is prepared from a single type of a dicot (e.g., broccoli), wherein the sprouts are harvested 3 days after germination (i.e., seed opening and/or protrusion of cotyledons or hypocotyls from seed shell). The plant material is then macerated, and optionally fermented, wherein fermentation is typically achieved by incubation of the macerated material with lactic acid bacteria for a period of about 24 hours at about 20° C. The so obtained macerated and optionally fermented plant material is then freeze-dried to form a powder, which may be employed as an ingredient in an alimentary product (e.g., food supplement, drink, etc.), or used directly in an oral formulation (e.g., tablet, capsule, syrup, etc.).

In another exemplary aspect of the inventive subject matter, various and distinct sprout preparations are prepared from two to eight species of dicots (e.g., alfalfa, broccoli, red clover, greens cress, cauliflower, Daikon radish, kale, yellow mustard, lentils, soy, and/or cabbage), wherein the sprouts are harvested 3 days after germination (i.e., seed opening and/or protrusion of cotyledons or hypocotyls from seed shell). The plant material is then processed as described above to obtain the sprout preparation.

Of course, it should be recognized that numerous dicot plants other than broccoli are also suitable for use herein, and particularly suitable plants include edible plants belonging to the family of Brassicaceae (formerly known as Cruciferaceae) and cultivars thereof. Therefore, and among other suitable plants for contemplated sprout preparations, especially preferred plants include *Armoracia rusticana* (Horseradish), *Barbarea vema* (Upland Cress), *Brassica carinata* (Abyssinian Mustard), *Brassica campestris* (Chinese group) Pak-Choi, *Brassica campestris* (Pekinensis group) Chinese Cabbage, *Brassica campestris* (Perviridis group) Spinach Mustard, *Brassica campestris* (Rapifera group) Turnip, *Brassica campestris* (Ruvo group), Broccoli Raab, *Brassica juncea* Brown and Indian Mustard, *Brassica napus* (Napobrassica group) Swede Turnip, *Brassica napus* (Pabularia group) Siberian Kale, *Brassica nigra* Black Mustard, *Brassica oleracea* var. *acephala* Collards, *Brassica oleracea* var. *botrytis* Cauliflower, *Brassica oleracea* var. *capitata* Cabbage, *Brassica oleracea* var. *fruticoca* Thousand-headed Kale, *Brassica olertacea* var. *gemmifera*, Brussel Sprouts, *Brassica oleracea* var. *gongylodes* Kohlrabi, *Brassica oleracea* var. *italica* Broccoli, *Crambe maritima* Sea Kale, *Eruca sativa* Roquette or Rocket Cross, *Lepidium meyenni* Maca, *Lepidium sativum* Land Cress, Pepper Grass, *Raphanus caudatus* Rat-tail Radish, *Raphanus sativus* Radish, *Raphanus sativus* (Longipinnatus group) Daikon or Chinese Radish, *Rorippa nasturtium-aquatikum* Water Cress, etc.

In further alternative aspects, numerous other edible dicots (e.g., belonging to the families of Fabaceae, Asteraceae, Chenopodiaceae, etc.) are also suitable for use in contemplated sprout preparations. For example, particularly preferred alternative dicot sprouts include bean sprouts, pea sprouts, soy sprouts, sunflower sprouts, quinoa sprouts, etc. Similarly, suitable sprouts also include monocot sprouts, and especially those belonging to the family of Poaceae. Thus, suitable monocot sprouts include oat sprouts, barley sprouts, millet sprouts, rye sprouts, corn sprouts, etc.

It is generally preferred that the plant seeds are first soaked or otherwise primed into a condition that triggers and/or accelerates sprouting. For example, in a typical process, seeds of one or more types of plants are soaked in water for a period of between about 2-16 hours and drained, and the so treated seeds are then placed onto a suitable substrate (e.g., drainage tray, hydroponic substrate, soil, etc.) and allowed to sprout. Most typically, the seeds will be exposed to indirect sunlight, but artificial illumination is also deemed suitable. In such case, a normal circadian illumination is preferred under conditions that provide quantum flux and spectral distribution similar to daylight. However, it should be noted that the light quality may also vary considerably. For example, where desirable a plant sprout may be cultivated under conditions that reduce total exposure to light or a spectral fraction thereof to delay or even prevent greening. Alternatively, the light may be filtered to remove red light components that are effective in triggering particular metabolic and/or developmental pathways. On the other hand, plant sprouts may also be grown under increased red or blue light such as to increase a plant response via red- and/or blue light receptors. Furthermore, it should be noted that the sprouts will be grown at about ambient temperature (e.g., between 15 and 25° C.) and atmosphere. However, where desired, the sprouts may also be grown at elevated (or reduced) temperature and/or modified atmospheric conditions (e.g., increased $CO_2$ content).

With respect to typical growth times for sprouts used in conjunction with the teachings presented herein, it is generally preferred that the sprouts are harvested after about two to five days post germination. The most suitable time for sprout harvest will typically depend on the particular seed type (species) and growth condition. Moreover, where a particular composition of the sprout preparation will be at least partially determined by the growth time allowed (content in cytokinins, pigments, sulfurophanes, etc.), such growth time may be determined by a person of ordinary skill in the art without undue experimentation. Such growth time may then be preferred. However, other developmental stages are also considered suitable and include perigerminative stages (e.g., pregermination stage, stage at which the seed opens, and/or stage at which the cotyledons and/or hypocotyls begin to protrude from the seed shell), stages in which the plant has not reached full chlorophyll synthesis, etiolated stages, and sprouts having secondary leaves (i.e., leaves other than the cotyledons). Thus, suitable plant sprouts are generally between one day and two weeks after germination (or more), and most typically between two and five days after germination.

With respect to the plant material used in contemplated sprout preparations, it is generally preferred that the plant material excludes non-germinated seeds, seed shells, husk, hull, or other remaining seed components. However, in certain aspects, and especially where the seed includes desirable components (e.g., cytokinins to modulate lipid and/or glucose metabolism; isoflavones to protect from oxidative damage, storage lipids or carbohydrates, etc.) the plant material will include at least a portion of the seed other than the sprout (e.g., root, husk, hull) or the entire seed (e.g., in non-germinated form that may or may not have been soaked or otherwise pretreated). Viewed from another perspective, the plant material in contemplated sprout preparations is advantageously enriched in a portion of at least one of the hypocotyls, the cotyledons, and the seed.

In preferred aspects, the plant material is macerated or otherwise disintegrated to release one or more components of a plant cell or plant organelle (e.g., vacuole, chloroplast, etioplast, etc.). All known manners of sprout and cell disintegration are deemed suitable and especially include milling, cutting, mashing, pressing, sonication, or any reasonable combination thereof, which may further be assisted by enzymatic digest (e.g., cellulase, protease, etc.). Alternatively, the sprouts may also be harvested and freeze dried (or otherwise at least partially dehydrated). In such case, the at least partially dehydrated material may be directly used as is or may further be comminuted to a desired average particle size. Regardless of the manner of disintegrating of the sprouts, it should be recognized that the optionally dehydrated sprouts can be processed to enrich for and/or remove a particular fraction or component. For example, solids can be removed via filtration or centrifugation, or one or more components can be extracted using solvent extraction, chromatography, etc.). It should be noted that all known manners of food processing are deemed suitable for such use and include ion exchange chromatography, affinity chromatography, solvent extraction with nutritionally acceptable solvents, size exclusion chromatography, etc. A person of ordinary skill in the art will readily be able to identify suitable processes that will preserve and/or concentrate the active ingredient effective in reduction of oxLDL formation. Of course, where desired, one or more functional and/or inactive ingredients may also be added to the sprouts before, during, and/or after processing. For example, and among other contemplated additional ingredients, especially suitable ingredients include vitamins, minerals, antioxidants, one or more phytosterols, betalains (betaxanthins and/or betacyanins) and/or other nutritionally beneficial substances. The amount of such additional ingredients will typically be between 1-10 wt % of the sprout preparation, in some cases between 10-40 wt % of the sprout preparation and in few cases between 41-99 wt % of the sprout preparation.

In another step, the sprouts (optionally comminuted or otherwise disintegrated) or the (optionally disintegrated and optionally dehydrated) sprout preparation may be fermented under aerobic and/or anaerobic conditions using one or more strains of a nutritionally acceptable microorganism. For example, contemplated microorganisms include various probiotic bacteria (e.g., *Lactobacillus* spec., *Bifidobacterium* spec., etc.) and yeasts (e.g., *Saccharomyces* spec., etc.). With respect to fermentation conditions and quantities of microorganisms employed, the same considerations as those known in the art apply. Among other beneficial uses, fermentation may advantageously be employed to remove sugar and/or lipids, transform a precursor component (e.g., glycosidic compound, carbohydrate, etc.) into a more desirable component (e.g., aglycon of the compound, alcohol, etc.), render a component more water soluble, etc. Still further, in at least some aspects of the inventive subject matter, fermentation may also increase the potential of the preparation to reduce oxLDL and/or increase HDL. Therefore, it should be recognized that the fermentation conditions may vary substantially and will predominantly depend on the microbial strain(s) employed, and the chemical nature of the bioconversion. However, and most typically, fermentation is performed for a period of between about 2 hours to 48 hours, typically at a temperature between about 10° C. and 60° C. (Preferred fermentations are typically batch processes that may be inoculated with a portion of a prior fermentation).

After optional fermentation, the disintegrated preparation (optionally treated) is at least partially dehydrated to form a syrup, paste, or dry solid that can then be converted into a desirable formulation. For example, suitable formulations include powders, solid comminuted material, etc., all of which may be supplied as a bulk material, included into an edible and/or drinkable product (e.g., cereal, snack bar, flavored beverage, etc.), or formulated into a oral dosage formulation (e.g., tablet, capsule, etc.). Alternatively, the Sprouts (macerated or whole) and/or the at least partially dehydrated preparation may be further processed using a solvent extraction process, preferably using a nutritionally acceptable solvent (e.g., ethanol, water, supercritical $CO_2$, etc., or mixtures thereof), a chromatographic step (size exclusion, affinity separation, ion exchange, etc.), a filtration step, a precipitation step, etc. to concentrate the preparation in one or more desirable ingredients and/or to remove one or more undesired ingredients. Contemplated sprout preparations are suitable for combination with edible carriers that may be solid (e.g., snack bars, cereals, prefabricated meal, etc.) or liquid (e.g., carbonated or still beverage, tea, fruit or vegetable juice, etc.) or may be packaged in a tablet, capsule, or powder form. Thus, nutritional supplements comprising contemplated sprout preparations are especially preferred. Alternatively, the sprout preparations may also be provided as bulk material (typically in quantities of at least 100 g, more typically at least 1 kg, and most typically at least 10 kg).

Of course, it should be recognized that contemplated sprout preparations may be prepared in separate batches in which each batch includes only one type of sprouts and wherein the final preparation is compounded from two or more distinct sprout preparations. Such process may be particularly advantageous where one sprout preparation requires removal of an ingredient that is not present in another preparation. On the other hand, suitable sprout preparations may also be prepared from a blend of distinct types of sprouts (e.g., alfalfa, water cress, red clover, broccoli) that are combined after harvest in desired proportions and that are freeze dried as a mixture, which is then ground up into a final combined sprout preparation without further processing.

In yet another aspect of the inventive subject matter, contemplated compositions and/or comestible compositions comprising same are administered to a mammal (and most preferably human) as a prophylactic and/or therapeutic composition to prevent and/or reduce formation of oxidized LDL. With respect to dosages, it is generally contemplated that the recommended daily dosage for contemplated sprout preparations will be in the range of between about 100 mg (e.g., where the sprout preparation is extracted or otherwise enriched for a desired ingredient) to about 50 g, and more typically between about 500 mg to about 25 g of the sprout preparation. Where a particular effect is desired with respect to reduction of oxidized LDL cholesterol and/or increase of HDL cholesterol, larger or smaller amounts are not excluded (see below). Most typically, the recommended daily dosage is administered between once and three times daily for a period of at least 1 day, more typically 7 days, even more typically 21 days, and most typically more than three weeks. Alternatively, it should be appreciated that dosage and administration schedules may be varied in response to measurement of oxidized LDL and/or HDL cholesterol levels in the mammal.

Therefore, the inventors also contemplate methods of marketing and/or advertising in which ingestion of contemplated compositions comprising sprout preparations described herein is associated with a reduction and/or prevention of LDL oxidation in a human. Optionally, further information may also be provided about an increase in HDL cholesterol associated with ingestion of the sprout preparations presented herein. Most typically the association is physically (e.g., on the package or container of the composition), but other associations, including displayed or printed are also deemed suitable. For example, a brochure or website may inform a customer about the reduction and/or prevention of LDL oxidation using contemplated compositions. Most typically, reduction of LDL oxidation is at least 5%, more typically at least 10%, even more typically at least 20%, and most typically at least 30% as compared to the average value determined prior to administration of contemplated compositions. Similarly, the increase in HDL cholesterol is typically at least 5%, more typically at least 10%, and even more typically at least 15% as compared to the average value determined prior to administration of contemplated compositions.

Therefore, and among other contemplated uses, it should be recognized that the compositions according to the inventive subject matter may be employed in a method of reducing oxidized LDL cholesterol in serum of a human. Most typically, such methods will include a step in which a combination of at least two preparations of two distinct dicot sprouts in form of a dietary supplement is administered to the human (preferably, combination is present in the supplement in an amount effective to reduce oxidized LDL cholesterol in human serum when orally administered to the human). In another step, the combination is present in the supplement in an amount effective to reduce oxidized LDL cholesterol in human serum when orally administered to the human, and in a still further step, the human is instructed to ingest the supplement at a recommended daily dosage that is effective to reduce oxidized LDL cholesterol in the human. Suitable daily dosages will depend on the particular formulation and optional processing. However, in most aspects, contemplated daily dosages are typically between 10 mg and 20 g, and more typically between 100 mg and 10 g. Particularly preferred dicot sprouts include alfalfa, red clover, green cress, broccoli, cauliflower, Daikon radish, kale, yellow mustard, soy, lentil, and cabbage, and at least one, and more typically at least two (e.g., between two and seven, eight, or even more) of the dicot sprouts are a cruciferous sprout (belonging to the family of Brassicaceae).

Therefore, a nutritional supplement product for measurable reduction of oxidized LDL cholesterol by at least 20% in human serum will preferably comprise a combination of at least two preparations of two distinct dicot sprouts, wherein the combination is present in the supplement in an amount effective to reduce oxidized LDL cholesterol in human serum when orally administered to the human. In such supplements, an information (printed, displayed, audible, etc.) is provided that oral administration of the supplement reduces oxidized LDL cholesterol.

EXAMPLES

All experiments were performed using a sprout preparation commercially available from Futureceuticals (819 N. Dixie Hwy, Momence, Ill. 60954) under the name SPROUTGARDEN™, which comprises a freeze-dried and powderized mixture of eight distinct sprouts (six of which belong to the family of Brassicaceae, and two of which belong to the family of Leguminosae), each sprout being present in a weight range of between 1-25 wt % to a total of 100%. Unless indicated otherwise, the powder was not further processed and used either as oral dietary supplement or as filtered aqueous solution. Ascorbic acid was used as a reference antioxidant under the same experimental conditions at various concentrations.

Long-Term Effect of Sprout Preparations on Ex Vivo LDL Oxidation

The method used in this experiment was based on fluorescent characteristics of oxLDL (see e.g., Fluorescent properties of oxidized human plasma LDLs. Singh et al. BBA, 1254, 135-139, 1995), which allowed the development of a quick and reliable method to measure formation of Cu-induced oxLDL directly in human serum substantially as previously described (A simple test for predisposition to LDL oxidation based on fluorescence development during copper-catalyzed oxidative modification. Cominacici et al. J Lipid Res, 32, 349-358, 1991. Oxidation of human LDLs results in derivatization of lysine residues of apolipoprotein B by lipid peroxide decomposition products. Steinbrecher, JBC, 262(8), 3603-3608, 1987. Comparison of three methods for measuring LDL resistance against copper-induced oxidation. Scheffer et al. Clin Chem. 46, 291-294, 2000). Here, an exemplary sprout preparation (SPG) and ascorbic acid (ASCA) were dissolved in $H_2O$ and tested at various concentrations to calculate IC50 (ug/mL), Results are depicted in FIGS. 1A and 1B reflecting preventive effects of SPG and ASCA after 2 and 16 hrs of serum exposure to copper ions, respectively. FIGS. 1C-1F depict fluorescence increase (fold) in the assay at 2 and 16 hours using SPG and ASCA, respectively.

Briefly, human serum was collected from a young, healthy individual. Total amounts of cholesterol, HDL, LDL, triglycerides were measured using Cholestech System. SPG in powder form was provided by VDF FutureCeuticals, Inc. and dissolved in water at various ad indicated concentrations. Copper chloride was from Sigma. Black transparent-bottom 96-well plates were from Nalgene Nunc International. Oxidation of LDL was measured using fluorescence methods as described elsewhere (supra). Cu-induced LDL oxidation was performed in PBS (100 ul/well) with 4 ul of human sera, 2 ul of copper chloride (concentration 4 mM) and 0.5 ul of $H_2O_2$ (concentration 88.2 nM) resulting in 8-uM concentration of copper ions and 44 μM of hydrogen peroxide, respectively. Formation of Cu-induced oxLDL was measured directly in human serum using a 96-well plate set up and Gemini Fluorescent plate reader (Molecular Devices). The fluorescence signal at 360/430 and 360/470 was measured at time 0, 2 and 16 hours. oxLDL fluorescence values compared to concentration 0 on each graph show how much fluorescent signal for oxidized LDL increased between time 0 and 2 or 16 hrs, respectively, while the value at concentration 0 represents the max increase of oxLDL generation under the experimental conditions. On average, the levels of oxidized LDL measured by fluorescence increased by 3 and 9 times after 2 and 16 hours, respectively.

As can be seen from the graphs, ascorbic acid prevented Cu-induced LDL oxidation in serum during the first 2 hrs [FIG. 1A, red line] (IC50=69 ug/ml), but not after 16 hrs, [FIG. 1B, red line]. In contrast, the preventive effect of SPG remains after longer exposure albeit at a somewhat reduced level. The apparent SPG IC50 after 2 hrs was 50 ug/mL (FIG. 1A, blue line) and after 16 hrs was 82 µg/mL (FIG. 1B, blue line). These results suggest that SPG contains chemically stable direct or indirect inhibitors of Cu-induced LDL oxidation. It should be noted that these inhibitors are water soluble since DMSO-based solutions showed significant inhibitory effect under these experimental conditions (data not shown). Taken together, the results of this experiment show that SPG inhibits LDL oxidation ex vivo more than ASCA following a 2 and 16 hour time course.

Thus, it should be recognized that SPG exhibits significant potency in prevention of Cu-induced LDL oxidation ex vivo. Moreover, the preventive effect of SPG is extended over time as compared to ascorbic acid Linder the same experimental conditions. This study suggests that SPG inhibits oxidation of LDL in human sera ex vivo. Collected results further showed that SPG inhibits Cu-induced LDL oxidation in a dose-dependent manner. The calculated IC50 value is 50 ug/mL. In comparison, ascorbic acid, (ASCA), under the same experimental conditions, inhibited LDL oxidation less efficiently with an $IC_{50}$ value of 69 ug/mL. It is therefore contemplated that SPG may contain active compounds, which at concentrations lower than ASCA, inhibit LDL oxidation ex vivo in a direct or indirect manner.

Inhibitory Effect of Sprout Preparations on In Vivo LDL Oxidation

Oxidized LDL (oxLDL) has been recognized as a prognostic marker of cardiovascular conditions (see e.g., Meisinger et al., Circulation, 2005, 112, 651-657). Additionally, still other studies have shown that oxLDL may trigger formation of foam cells and plaques (e.g., Young et al. Biochem Soc Trans., 2001, 29, 358-362). Thus, the prevention and reduction of oxLDL blood levels have become targets for development of anti-oxLDL treatments, functional food products and supplements that help prevent development of cardiovascular pathologies. Published studies have shown that LDL oxidation could be reduced by pomegranate (see e.g., Wang et al. J Nat Prod., 2004, 67, 2096-8), almonds (see e.g., Circulation., 2002, 106, 1327-32), and grapes (Free Radical Res., 2003, 37, 573-84). According to Lapointe, nutritional interventions appear to play a key role in modulation of oxLDL levels in the bloodstream (Lapointe et al., J. Nutr., 2005, 135, 410-415). Based on our earlier studies (supra) that showed that SPG can prevent copper-induced LDL oxidation in human serum SPG was tested in three individuals having increased serum levels of oxLDL prior to consumption of SPG.

SPG was provided as above by VDF FutureCeuticals, Inc, Momence, Ill., USA and SPG was analyzed for content of total isothiocyanates and total sulforaphane. All participants were provided with consent forms and advised about GRM and purpose of the study. Subsequently, the participants were screened for oxLDL levels in blood. Three individuals with oxLDL levels above 100 U/L were selected for these studies. All participants were advised to maintain typical diet, medicines and habits during the study. SPG was orally administered as aqueous suspension twice daily with 5 g per dose for 21 days. Serum analysis of oxLDL was measured before and after the treatment using oxLDL Elisa from Mercola. LDL, Glucose, AST, and ALT were measured using Cholestech Cassette System. 8-Isoprostanes were measured using Elisa from Assay Design, Inc.

Blood analyses showed that oxLDL was reduced in each individual by 90, 42, and 71% respectively. In parallel, blood levels of 8-isoprostanes and total peroxides were also reduced (but to a lesser extent) as presented in FIG. 2. Other parameters (LDL, glucose, AST, ALT) remained within normal ranges (data not shown). It should be especially noted that this is the first report suggesting that dicot, and especially cruciferous sprouts may reduce oxLDL in humans. Cruciferous seed sprouts are known to induce phase 2 proteins (P2P) due to the presence of various isothiocyanates. Without wishing to be bound by any theory or hypothesis, it is contemplated that inducers of phase II enzymes may have at least partially contributed to the reduction of oxLDL in the study participants. However, it should also be noted that various other compounds in sprouted cruciferous seeds may inhibit oxLDL oxidation without affecting phase II enzymes. Still further, it should be noted that the total ORAC value of SPG was in almost all preparations less than 250, more typically less than 200, and most typically less than 150, which strongly suggests that SPG prevents oxLDL formation by a mechanism other than radical scavenging (which is likely independent of amount of antioxidants). In contrast, fruits such as prunes have an ORAC of about 5700, blueberries of about 2400, and oranges of about 750. Therefore, the possible mechanism of action of SPG to reduce oxLDL remains unknown at this time.

Consequently, reduction of oxLDL in human serum using contemplated compositions and methods is typically at least between 5% and 15%, more typically at least 20%, even more typically at least 40%, and most typically at least 50% when the preparation is administered over at least 10 days, and more typically over at least three weeks.

Stimulating Effect of Sprout Preparations on In Vivo HDL Formation

Currently, five different types of treatments are recognized to increase serum HDL in human: Statins, niacin, fibrates, bile acid sequestrants, and cholesterol absorption inhibitors (see e.g., Curr Atherosclerosis Rep., 2005, 7, 88-94). Recent peer-reviewed publications have also shown that certain natural products may increase blood HDL, including dark chocolate (Mursu et al., Free Radical Biology & Medicine, 2004, 37, 1351-1359). Study of food-based products to increase HDL or to prevent its reduction is ongoing in our laboratory. SPG, one such food-based product, was used in four independent cases to test its effect on HDL blood levels.

All volunteers recruited for this study had initial HDL blood level below 40. All volunteers consumed 5 g of SPG twice per day for three weeks. Following blood analyses it was found that HDL-Cholesterol levels were increased in each individual by an average of 29%. Other parameters (LDL, glucose, AST, ALT) Monitored in this study remained within normal range. Again, SPG was provided by VDF FutureCeuticals, Inc, Momence, Ill. and analyzed for content of total isothiocyanates and total sulforaphane. Participants were provided with consent forms and advised about GRM and the purpose of this study. Subsequently, participants were screened for HDL levels in blood. Four individuals with HDL levels below 40 mg/dL were selected for these studies. All participants were advised to maintain typical diet, medicines and habits during the study. SPG was orally administered as aqueous suspension twice per day with 5 g per dose for 21 days. Blood levels of HDL, fasting glucose levels, LDL, ALT, AST, and triglycerides were measured before and after the treatment using Cholestech Cassette System.

Figure 3:
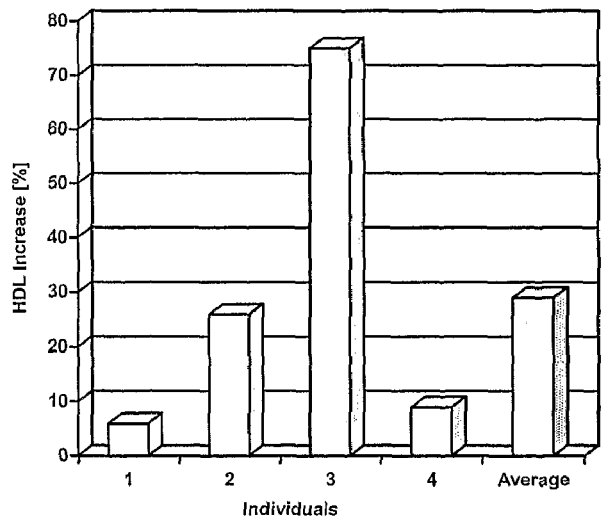
FIG. 3 is a graph indicating increase of in vivo serum HDL in response to oral administration of contemplated compositions in human.

Remarkably, the inventor discovered that SPG significantly increases HDL in a wide range of response among all volunteers. All volunteers showed an increase of HDL in blood after consumption of SPG as illustrated by the graph in FIG. 3. Three weeks use of SPG increased blood levels of HDL by an average of 29%. Other parameters such as LDL, fasted glucose, AST and ALT remained within normal ranges. Collected results show that all volunteers participating in the studies experienced varying and individualized degrees of increased levels of HDL. Table I below depicts the results from a low dose study in which 3 g/70 kg of SPG were given over a period of 2 weeks. Again, individual results varied, but exhibited a significant upward trend of HDL in response to SPG administration.

TABLE 1

| Volunteer | Initial HDL [mg/dl] | HDL Week 1 | HDL Week 2 | % Increase |
|---|---|---|---|---|
| 1 | 43 | 52 | 49 | +14 |
| 2 | 20 | 21 | 23 | +15 |
| 3 | 47 | 43 | 43 | −9 |
| 4 | 36 | 34 | 43 | +19 |
| 5 | 26 | 25 | 26 | 0 |

Consequently, increase of HDL in human serum using contemplated compositions and methods is typically between 2% and 35%, more typically at least 5-6%, even more typically at least 6-10%, and most typically at least 11% when the preparation is administered over at least 10 days, and more typically over at least three weeks. Therefore, it should be particularly appreciated that contemplated compositions and methods are effective not only to substantially reduce oxLDL levels in serum upon oral administration, but also effective to raise serum HDL levels. Viewed from another perspective, it is therefore contemplated that the compositions and methods according to the inventive subject matter may be employed to increase the numeric ratio of HDL (expressed in mg/dl) to oxLDL expressed in U/l) in an amount of at least 5%, more typically at least 10%, more typically at least 30%, and most typically at least 50%. While not wishing to be bound by any specific theory or hypothesis, the inventors contemplate that the increase in HDL may also to at least some degree contribute to a reduction of oxLDL.

Contemplated Compositions Increase Phase II Proteins In Vitro

High activity of phase II proteins was reported to play an important role in prevention of cancer (Cancer Epid, Biomarkers & Prevention, 2001, 10, 501-508), including stomach and lung cancer (J Agric Food Chem., 2005, 53, 8993-96) and UV-induced skin carcinogenesis (Cancer Letters, 2005). Other studies show that inducers of phase II proteins are important in management of cardiovascular conditions including hypertension (PNAS, 101, 7094-7099), aging of central nervous system (Nutr Neurosci, 8, 101-110), cerebral edema caused by trauma, and photooxidative damage of retina. Further reports indicated that consumption of 100 g of fresh broccoli sprouts (rich in P2P inducers) significantly reduces blood levels of 8-isoprostanes (Biofactors, 2004, 22, 271-275), which are considered markers of oxidative stress. Most phase II proteins (e.g., quinone reductase-1, glutathione transferase, epoxide hydrolase, heme oxigenase) are thought to play key roles in scavenging and inactivation of harmful chemicals and reactive oxygen species (ROS) and are regulated by Antioxidant Responsive Elements (ARE) in their promoter region.

SPG was analyzed for isothiocyanate and sulfurophane content prior to this study and then analyzed for its potency to increase production of phase II enzymes. Analytical data showed that amount of glucosinolates, isothiocyanates, and sulfurophanes was 20 mg/g, 14.2 mg/g, and 4 mg/g, respectively. Other chemical analyses of SPG showed high content of total amino acids (24%), low concentration of total sugars (1.55%), and low amount of sodium (0.2 mg/g). Among amino acids, glutamic acid was found at highest concentration (48 mg/g), and histidine at the lowest (8.6 mg/g). Calcium, magnesium, phosphorus, and potassium were found in amounts of 5.4 mg/g, 3.5 mg/g, 4.3 mg/g and 5.1 mg/g, respectively. These results represent the rather unique chemical composition of SPG. Phase II enzyme activity was measured as described by Prochashka (Anal. Biochem. 1988, 169, 328-336) using Hepa 1c1c7 cells in 96-well plates.

Figure 4:
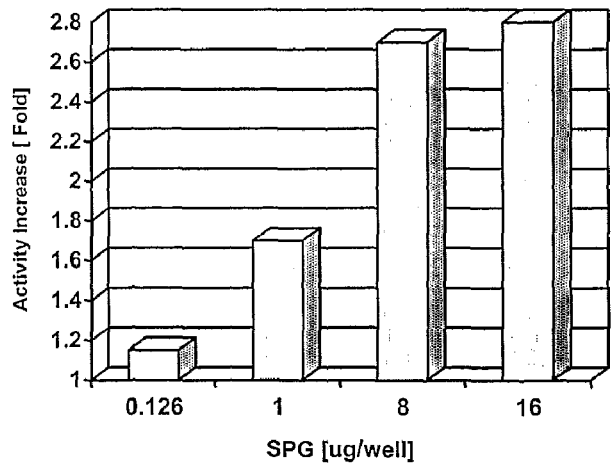
FIG. 4 is a graph indicating increase of phase II enzyme in vitro in human Hepa cells in response to addition of contemplated compositions.

Briefly, testing of SPG for stimulation of phase II enzymes was performed on Hepa 1c1c7 cells by following activity of QR-1, a commonly-used cellular model for testing phase II enzyme activity. Stock solution of the tested material was freshly prepared and used to treat a culture of Hepa cells at various concentrations over a period of 24 hrs. As can be taken from FIG. 4, the results showed a dose-dependent stimulation of QR-1 by SPG. At SPG concentration of 16 ug, QR-1 activity was induced by 2.8 times. Higher concentration did not show further stimulation of QR-1 due to an excess of tested material in the culture media under these experimental conditions. Therefore, it should be recognized that SPG could be used to treat various phase II enzyme dependent health conditions.

Thus, specific embodiments and applications of compositions and methods for reduction of LDL oxidation have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Furthermore, where a definition or use of a term in a reference, which is incorporated by reference herein is inconsistent or contrary to the definition of that term provided herein, the definition of that term provided herein applies and the definition of that term in the reference does not apply.

What is claimed is:

1. A method of reducing LDL cholesterol oxidation in a human in need thereof comprising administering therapeutically effective amounts of at least two sprouts selected from the group consisting of red clover, green cress, cauliflower, daikon radish, kale, yellow mustard, soybean, lentil and cabbage.

2. The method of claim 1 wherein the sprouts are dehydrated and lyophilized.

3. The method of claim 1, wherein the administering reduces oxidized LDL cholesterol in the human in need thereof by at least 20% when administered over at least 10 days.

4. The method of claim 1, wherein the administering increases HDL cholesterol in the human by at least 6% when administered over at least 10 days.

5. The method of claim 1, wherein the therapeutically effective amounts are effective to increase the numerical ratio of HDL mg/dl to oxidized LDL U/l in the human in need thereof by at least 2%.

* * * * *